(12) United States Patent  
Matsuki et al.

(10) Patent No.: US 11,964,446 B2  
(45) Date of Patent: Apr. 23, 2024

(54) CONTINUOUS PRODUCTION SYSTEM AND CONTINUOUS PRODUCTION METHOD

(71) Applicant: Mitsubishi Chemical Engineering Corporation, Tokyo (JP)

(72) Inventors: Akihiro Matsuki, Tokyo (JP); Nobuhiro Tanaka, Tokyo (JP); Katsuhiro Murata, Tokyo (JP); Hironobu Takeda, Tokyo (JP)

(73) Assignee: MITSUBISHI CHEMICAL ENGINEERING CORPORATION, Tokyo (JP)

( * ) Notice: Subject to any disclaimer, the term of this patent is extended or adjusted under 35 U.S.C. 154(b) by 383 days.

(21) Appl. No.: 17/416,238

(22) PCT Filed: Dec. 19, 2019

(86) PCT No.: PCT/JP2019/049877  
§ 371 (c)(1),  
(2) Date: Jun. 18, 2021

(87) PCT Pub. No.: WO2020/130088  
PCT Pub. Date: Jun. 25, 2020

(65) Prior Publication Data  
US 2022/0072821 A1 Mar. 10, 2022

(30) Foreign Application Priority Data  
Dec. 19, 2018 (JP) .................. 2018-237253

(51) Int. Cl.  
*A61J 3/10* (2006.01)  
*A61K 9/20* (2006.01)  
(Continued)

(52) U.S. Cl.  
CPC ........ *B30B 15/0082* (2013.01); *A61K 9/2095* (2013.01); *B08B 5/02* (2013.01);  
(Continued)

(58) Field of Classification Search  
CPC . A61J 3/10; A61K 9/2095; B08B 5/00; B08B 5/02; B08B 9/027; B08B 9/032;  
(Continued)

(56) References Cited

U.S. PATENT DOCUMENTS 5,558,472 A * 9/1996 Ogawa ................. B65G 53/521  
406/197  
2014/0356079 A1 12/2014 Rusterholz  
(Continued)

FOREIGN PATENT DOCUMENTS

JP      H07-047372 Y2    11/1995  
JP      H11-030345 A     2/1999  
(Continued)

OTHER PUBLICATIONS

Extended European Search Report issued in EP Application No. 19898681.2, dated Sep. 14, 2022.  
(Continued)

*Primary Examiner* — Leo B Tentoni  
(74) *Attorney, Agent, or Firm* — Knobbe Marten Olson & Bear LLP (57) ABSTRACT

A continuous production system continuously produces a product from a raw material powder. The system includes a first processor that performs a first process on the raw material powder, a second processor that performs a second process on the powder on which the first process has been performed by the first processor, and a test chamber through which the powder being sent from the first processor to the second processor passes. A cleaner blows gas from an inlet side opening formed in the inner face of a channel connected to the test chamber from the first processor on the downstream side of an inlet side gate valve for opening and closing the channel toward a direction to form a swirling flow along the inner face of the channel.

7 Claims, 7 Drawing Sheets

(51) Int. Cl.
  *B08B 5/02* (2006.01)
  *B08B 9/027* (2006.01)
  *B08B 9/032* (2006.01)
  *B08B 9/093* (2006.01)
  *B30B 11/00* (2006.01)
  *B30B 11/16* (2006.01)
  *B30B 15/00* (2006.01)
  *B65G 53/02* (2006.01)
  *B65G 53/46* (2006.01)
  *B65G 53/52* (2006.01)
  *B65G 53/54* (2006.01)
  *B65G 53/56* (2006.01)
  *B65G 53/66* (2006.01)
  *G01N 1/20* (2006.01)

(52) U.S. Cl.
  CPC .......... *B08B 9/0321* (2013.01); *B08B 9/0325* (2013.01); *B30B 11/005* (2013.01); *B65G 53/4691* (2013.01); *B65G 53/52* (2013.01); *B65G 53/521* (2013.01); *G01N 1/2035* (2013.01); *B08B 2209/08* (2013.01); *B65G 2201/042* (2013.01); *G01N 2001/205* (2013.01); *G01N 2001/2057* (2013.01)

(58) Field of Classification Search
  CPC ..... B08B 9/0321; B08B 9/0325; B08B 9/093; B08B 2209/08; B30B 11/005; B30B 11/16; B65G 53/02; B65G 53/4691; B65G 53/521; B65G 53/54; B65G 53/56; B65G 53/66; B65G 2201/42; G01N 1/20; G01N 1/2035; G01N 2001/205; G01N 2001/2057; G01N 33/15

USPC ........ 264/39, 40.1, 109, 406, 409; 425/80.1, 425/135, 406; 134/18, 22.1, 22.11, 22.12, 134/37, 56 R, 166 C, 166 R, 169 C, 198; 406/183, 197

See application file for complete search history.

(56) References Cited

U.S. PATENT DOCUMENTS

2018/0056332 A1    3/2018   Fuchigami et al.
2020/0397658 A1   12/2020   Matsuki et al.

FOREIGN PATENT DOCUMENTS

| JP | 3916230 B2 | 5/2007 |
| JP | 4472494 B2 | 6/2010 |
| JP | 5794904 B2 | 10/2015 |
| JP | 5798400 B2 | 10/2015 |
| JP | 5805482 B2 | 11/2015 |
| JP | 2018-034113 A | 3/2018 |
| WO | WO 2019/163059 A1 | 8/2019 |

OTHER PUBLICATIONS

Corrected Written Opinion and Annexes of EP Application No. 19898681.2, dated Sep. 26, 2022.
International Search Report issued in International Application No. PCT/JP2019/049877, dated Feb. 10, 2020.

* cited by examiner

FIG. 7 ously a product from powder raw materials, and the quality of the product is managed by analyzing powder collected in this inspection chamber. However, in order to detect quality defects in this inspection chamber of such a device configuration and to discharge powder of defective quality from the inspection chamber so that there is no intermingling thereof with other powder, a configuration needs to be made in which there is no powder retained in the inspection chamber. However, the inspection chamber has parts such as valves for closing off entrance and exit ports, and so forth, and powder is readily retained at the valves and the proximity thereof in this structure.
CONTINUOUS PRODUCTION SYSTEM AND CONTINUOUS PRODUCTION METHOD

TECHNICAL FIELD

The present invention relates to a continuous production system and a continuous production method.

BACKGROUND ART

Various types of inspection are performed to maintain product quality in manufacturing pharmaceuticals and food products, for example. In manufacturing of pharmaceutical tablets, for example, in order to obtain tablets of a predetermined hardness, the moisture content of a powder or granular material manufactured by using a granulator and a dryer is measured before entering into a tablet press (e.g., see PTL 1).

DOCUMENTS OF PRIOR ARTS PATENT DOCUMENT

[PTL 1] Japanese Patent No. 5798400

SUMMARY OF THE INVENTION

Problems to be Solved by the Invention

At a manufacturing site that handles powdery raw materials, devices that handle various processes such as mixing, granulating, and drying, are each prepared, and containers are used for moving the raw materials (hereinafter also including "intermediate products") between the processes. In this type of manufacturing method, also called batch production, inspection preformed to maintain product quality is carried out by, for example, taking a sample out of the container containing the raw materials. In a case where the inspection results indicate that the sample is defective, for example, the raw materials in the container from which the sample was taken are discarded.

However, in the case of batch production, once a sample is determined to be defective, all raw materials in the container from which the sample was taken are determined to be defective and are discarded, regardless of the possibility that non-defective raw materials might coexist. Accordingly, it is desirable to manufacture pharmaceuticals and food products by continuous production, in which parameters of manufacturing processes are automatically controlled, so that no quality defects occur. In order to perform automatic control of parameters in manufacturing processes for continuous production of pharmaceuticals and food products appropriately, there is a need to continuously measure parameters relating to quality with high precision. However, parameters such as hardness and solubility, for example, cannot be directly measured by continuous non-destructive measurement. Accordingly, for parameters such as hardness and solubility that cannot be directly measured by continuous non-destructive measurement, a technique is employed which indirectly manages quality using other parameters that have relevancy regarding these parameters, such as moisture, particle size distribution, lubricant content, and so forth. In a case of measuring parameters such as moisture and particle size distribution by spectroanalysis, for example, suppression of disturbances that reduce measurement precision, such as change in bulk density of the powder, which is the object of measurement, is important. Also, in a case of measuring quality by optical unit, adhesion of powder to a measurement portion of, for example, a sight glass may cause reduction in measurement precision. Also, in a case where a quality defect is detected from a measured parameter in continuous production, a portion with defective quality in the manufacturing process needs to be promptly discharged before intermingling with other portions.

A configuration is conceivable in which an inspection and screening device that has an inspection chamber, through which the powder passes, is provided partway along the system for producing continu Accordingly, it is an object of the present invention to provide a technology that maximally suppresses retention of powder in a device for powder inspection that is provided partway along a system for producing continuously a product from powder raw materials.

Means for Solving the Problems

In order to solve the above problem, in the present invention, a cleansing mechanism is provided that, at a downstream side of an entrance-side gate valve of an inspection chamber, sprays gas in a direction forming a spiral flow following the inner face of a path.

Specifically, the present invention is a continuous production system producing continuously a product from a powder of a raw material, and includes a first processing device that performs first processing on the powder of the raw material, a second processing device that performs second processing on the powder, on which the first processing device has performed the first processing, and an inspection and screening device that has an inspection chamber through which powder fed from the first processing device to the second processing device passes. The inspection and screening device has a cleansing mechanism that, at a downstream side of an entrance-side gate valve that opens and closes a path connecting from the first processing device to the inspection chamber, sprays gas from an entrance-side opening formed on an inner face of the path in a direction forming a spiral flow following the inner face of the path.

According to such a continuous production system, a spiral flow is generated following the inner face of the path at the downstream side of the entrance-side gate valve, and accordingly around the entrance-side gate valve, where powder is readily retained, is cleansed by the spiral flow. Also, a spiral flow is generated following the inner face of the path at the downstream side of the entrance-side gate valve, and accordingly air flows thoroughly throughout the path, without generating any low flow rate regions formed due to stagnation of air in the path where the powder passes. Accordingly, portions, at which the air for cleansing does not reach and cleansing becomes defective, are not readily formed in the path where the powder passes. Thus, according to this continuous production system, retention of powder in the inspection and screening device can be maximally suppressed.

Note that the cleansing mechanism may spray gas from the entrance-side opening formed directly below the entrance-side gate valve in a direction forming a spiral flow following the inner face of the path. In a form in which gas is sprayed from the entrance-side opening directly below the entrance-side gate valve, powder adhering at a lower portion of the entrance-side gate valve is readily blown away.

Also, the cleansing mechanism may spray gas from the entrance-side opening in a state in which an exit-side gate valve that opens and closes a path on an exit side of the inspection chamber is open. By performing cleansing in a state in which the exit-side gate valve is open, powder retained in the inspection chamber can be blown away by the cleansing gas on the downstream side of the exit-side gate valve.

Also, the exit-side gate valve may have an elastic tube that forms part of a path connecting from the inspection chamber to the second processing device, and an opening/closing mechanism portion that clamps the tube to close off the path within the tube, with the cleansing mechanism spraying gas from the entrance-side opening in a state in which clamping of the tube by the opening/closing mechanism portion is released. A configuration that closes off the path by clamping the tube basically does not form any structural obstructions in the powder path in a state in which the valve is open. Accordingly, around the exit-side gate valve can also be cleansed by cleansing performed in a state with the exit-side gate valve open.

Also, the cleansing mechanism may further spray gas from an exit-side opening formed directly below the exit-side gate valve in a direction forming a spiral flow following the inner face of the path. Spraying air for cleansing from such a position as well enables the downstream side of the exit-side gate valve to be cleansed as well.

Also, the cleansing mechanism may spray gas from the exit-side opening in a state in which the exit-side gate valve is closed. According to this configuration, powder retained around the exit-side gate valve does not flow to the inspection chamber side, and accordingly powder retained in the inspection and screening device can be maximally suppressed.

Also, the inspection and screening device may have, on further a downstream side from the exit-side gate valve, channel switching unit for switching a discharge path of the inspection chamber between a path connecting from the inspection chamber to the second processing device, and a path connecting from the inspection chamber to other than the second processing device. According to this configuration, the destination of powder can be switched, and accordingly processing of powder in accordance with inspection results at the inspection chamber can be performed.

Also, the present invention can be understood from a perspective of a method. For example, the present invention may be a continuous production method producing continuously a product from a powder of a raw material in a continuous production system having a first processing device that performs first processing on the powder of the raw material, a second processing device that performs second processing on the powder, on which the first processing device has performed the first processing, and an inspection and screening device that has an inspection chamber through which powder fed from the first processing device to the second processing device passes, the method executing cleansing processing of spraying, at a downstream side of an entrance-side gate valve that opens and closes a path connecting from the first processing device to the inspection chamber, gas from an entrance-side opening formed on an inner face of the path in a direction forming a spiral flow following the inner face of the path.

Effects of the Invention

According to the above continuous production system and continuous production method, retention of powder can be maximally suppressed in a device for powder inspection that is provided partway along a system for producing continuously a product from powder raw materials.

DETAILED DESCRIPTION OF THE PREFERRED EMBODIMENT

An embodiment will be described below. The embodiment described below is only exemplary, and the technical scope of the present disclosure is not limited to the following form.

<Hardware Configuration>

Figure 1:
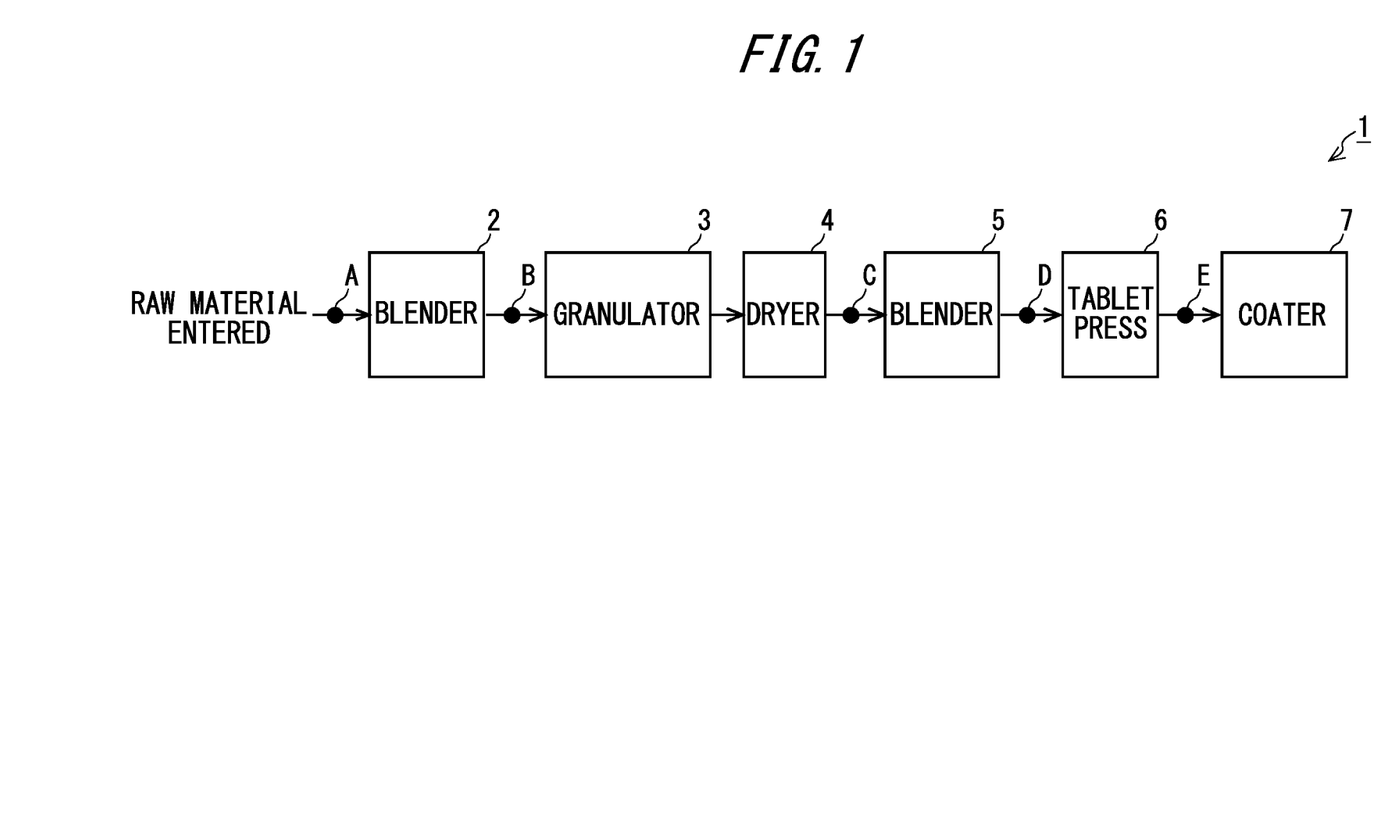
FIG. 1 is a diagram illustrating a continuous production system according to an embodiment.

FIG. 1 is a diagram illustrating a continuous production system 1 according to the embodiment. Although the present embodiment will be described with regard to an example of manufacturing pharmaceuticals, application can be made to manufacturing of, for example, food products and other types of products as well. The continuous production system 1 is a system for producing tables from powder raw materials, and is provided with a blender 2, a granulator 3, a dryer 4, a blender 5, a tablet press 6, and a coater 7, as illustrated in FIG. 1. The blender 2 has an inlet through which powder raw materials enter, and blends various types of powder that are raw materials for tablets. The granulator 3 adds water or a binder liquid to the raw materials blended by the blender 2, causing aggregation to small-particle nuclei and forming granules. The dryer 4 brings the raw materials granulated by the granulator 3 into contact with warm air so as to dry. The blender 5 adds a lubricant to the granulated raw materials dried by the dryer 4, and performs blending thereof. The tablet press 6 compresses the granulated raw materials blended by the blender 5 into a mold form, thereby forming tablets. The coater 7 subjects the tablets solidified by the tablet press 6 to coating. In the continuous production system 1, a series of facilities from the blender 2 to the coater 7 is connected. Accordingly, in the continuous production system 1, the raw materials entering the blender 2 are continuously subjected to the various types of processing performed by each in the series of facilities from the blender 2 to the coater 7.

Note that while FIG. 1 illustrates one piece of equipment each in the series from the blender 2 to the coater 7, the continuous production system 1 is not limited to this form. For example, an arrangement may be made in which one or a plurality of the blender 2, the granulator 3, and the dryer 4 are provided, with a plurality of types of raw materials being blended by the blender 5.

The series of facilities from the blender 2 to the coater 7 is controlled by an unshown control device that is provided to the continuous production system 1. The control device decides operation amounts of each piece of equipment on the basis of measurement values of various types of sensors provided to the continuous production system 1. Examples of measurement values that the control device references include values obtained from each piece of equipment from the blender 2 to the coater 7, such as the rotation speed of a screw feeder provided to the blender 2, the temperature in the dryer 4, and so forth, and further include values obtained from sensors provided along the path connecting the equipment. Examples of positions of sensors provided partway along the path connecting the equipment include positions such as indicated by signs A through E in FIG. 1. Providing a sensor at the sign C partway along the path connecting the dryer 4 and the blender 5 enables the control device to change the operation amount of the granulator 3 or the blender 5 depending on the state of the raw materials exiting the dryer 4, for example. Also, providing a sensor at the sign C partway along the path connecting the dryer 4 and the blender 5, for example, enables the control device to change the destination of the raw materials exiting the dryer 4 to other than the blender 5, depending on the state thereof, for example.

Figure 2:
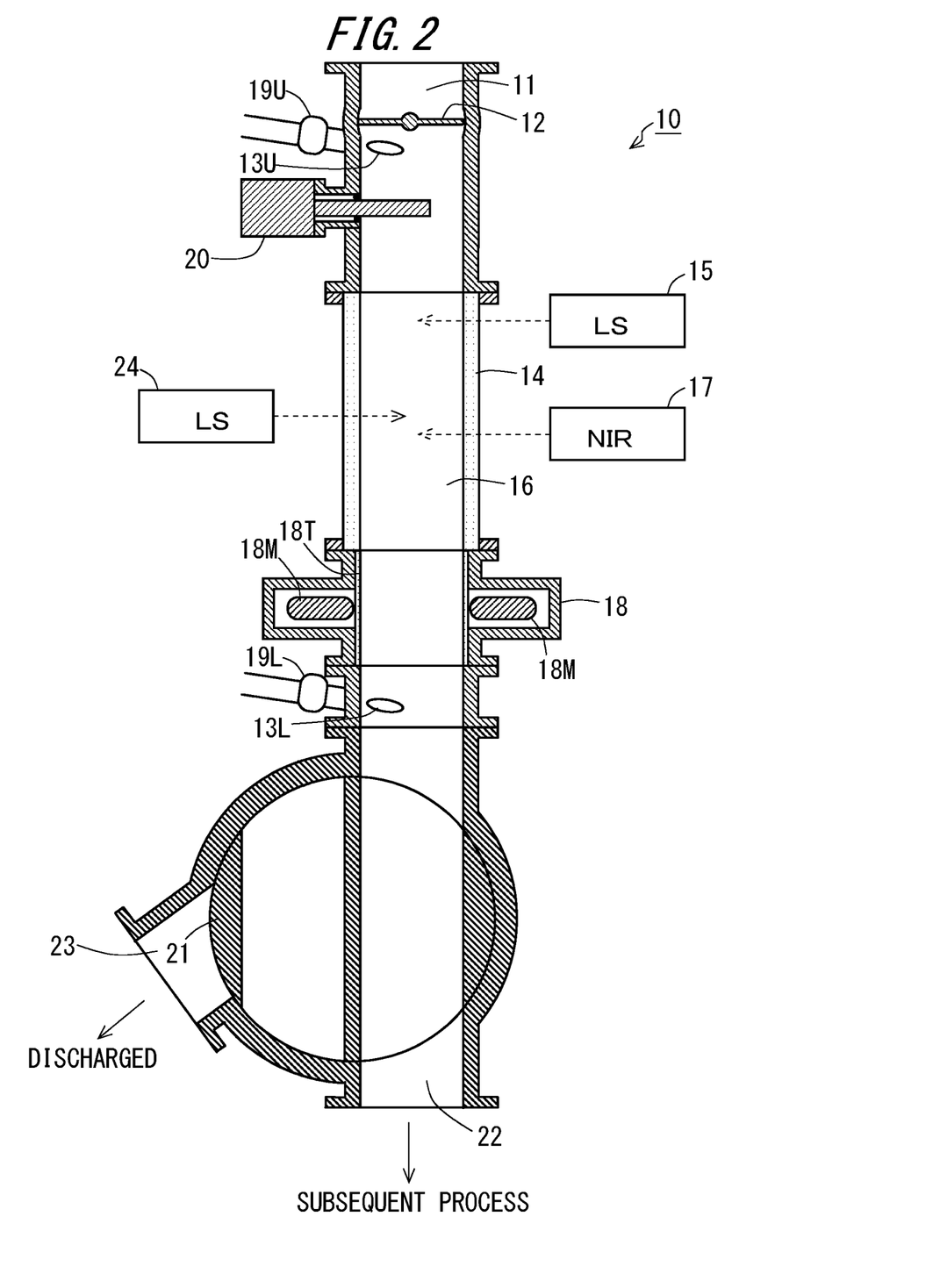
FIG. 2 is a diagram illustrating an example of an inspection and screening device provided to the continuous production system.

FIG. 2 is a diagram illustrating an example of an inspection and screening device 10 provided to the continuous production system 1. The inspection and screening device 10 can be provided to an appropriate position in the continuous production system 1. The inspection and screening device 10 is provided partway along the path connecting the equipment from the blender 2 to the coater 7, such as indicated by signals A to E in FIG. 1, for example.

The inspection and screening device 10 is provided with an inlet path 11 where raw materials fed from equipment connected to the upstream side of the inspection and screening device 10 enter, an entrance-side gate valve 12 disposed at the lower end of the inlet path 11, an inspection chamber 16 formed at the lower side of the entrance-side gate valve 12, an opening 13U on an air spray path formed directly below the entrance-side gate valve 12 (an example of an "entrance-side opening" in the present application), a sight glass 14 that makes up a wall face of the inspection chamber 16 and enables the inside of the inspection chamber 16 to be visible from around, an exit-side gate valve 18 disposed at the lower portion of the sight glass 14, and an opening 13L on an air spray path formed directly below the exit-side gate valve 18 (an example of an "exit-side opening" in the present application). Above the inspection chamber 16 is provided a particle size distribution measurement device 20 that measures particle size distribution of powder passing through. A probe of the particle size distribution measurement device 20 is inserted through a hole provided in a tube making up the wall face of the inspection chamber 16. In order to prevent raw materials from entering, a gap between this hole and the probe may be sealed by a sealing member, or may be set to a positive pressure by inflow of a slight airflow. Also, provided around the inspection chamber 16 are laser sensors 15 and 24 and a spectroanalysis instrument 17 that perform optical measurement of the inside of the inspection chamber 16 through the sight glass 14. Air sprayed into the path from the openings 13U and 13L is controlled by opening/closing operations of solenoid valves 19U and 19L (an example of "cleansing mechanism" in the present application) that shut off paths of high-pressure air supplied to the inspection and screening device 10. Note that the gas sprayed from the openings 13U and 13L is not limited to air, and may be inert gas or a gas of various other types of components.

The entrance-side gate valve 12 is a butterfly valve of which a valve element is circular, and is opened/closed by an unshown control device. The opening 13U is formed on an inner face of the path, near a valve chamber of the entrance-side gate valve 12. Due to the entrance-side gate valve 12 being a circular butterfly valve, the inside of the valve chamber has an inner circumferential face, and gas sprayed out from the opening 13U is sprayed out in a direction forming a spiral flow following the inner circumferential face of the path where the powder passes, and thus becomes a spiral flow where the powder flows along the path following the inner circumferential face of the path. Note that the entrance-side gate valve 12 is not limited to a butterfly valve, and may be a choke valve, for example, or any of various other types of valves.

The exit-side gate valve 18 has an elastic tube 18T that forms part of a path connecting from the inspection chamber 16 to the equipment on the downstream side of the inspection and screening device 10, and an opening/closing mechanism 18M (an example of an "opening/closing mechanism portion" in the present application) that clamps the tube 18T to close off the path within the tube 18T. The tube 18T has a cylindrical form, forming a path therein where powder passes. The exit-side gate valve 18 is a valve that clamps the tube 18T by the opening/closing mechanism 18M to close off the powder path, and accordingly basically does not form any structural obstructions in the powder path when in an open state. The exit-side gate valve 18 has a form in which the tube 18T is clamped by the opening/closing mechanism 18M to close the valve, and accordingly there are no fine gaps or the like through which power might enter into the path where the powder passes. Accordingly, it can be said that the exit-side gate valve 18 is a valve with a structure in which the possibility of powder being retained is low. Note that the exit-side gate valve 18 is not limited to such a form, and may be a choke value for example, or any of other various types of valves.

In the inspection and screening device 10, when raw materials are fed from equipment connected to the upstream side of the inspection and screening device 10 in a state in which the entrance-side gate valve 12 is in an open state and the exit-side gate valve 18 is in a closed state, the raw materials accumulate within the inspection chamber 16. While raw materials are being fed to the inspection chamber 16 from the equipment connected to the upstream side of the inspection and screening device 10, measurement of particle size is performed by the particle size distribution measurement device 20 in the inspection and screening device 10. When the laser sensor 15 detects that a predetermined amount of raw materials has accumulated within the inspection chamber 16, the entrance-side gate valve 12 is closed, and inspection of the raw materials is performed using the spectroanalysis instrument 17. A channel switching valve 21 (an example of "channel switching unit" in the present application) is provided on the lower side of the exit-side gate valve 18, and raw materials following inspection are fed to an outlet channel 22 or an outlet channel 23, in accordance with inspection results. Whether there are any raw materials retained within the inspection chamber 16 is inspected by the laser sensor 24. Note that while description is made in the present embodiment regarding an example using a near-infrared sensor as an example of the spectroanalysis instrument 17, the continuous production system disclosed in the present application is not limited to such a form.

Figure 3:
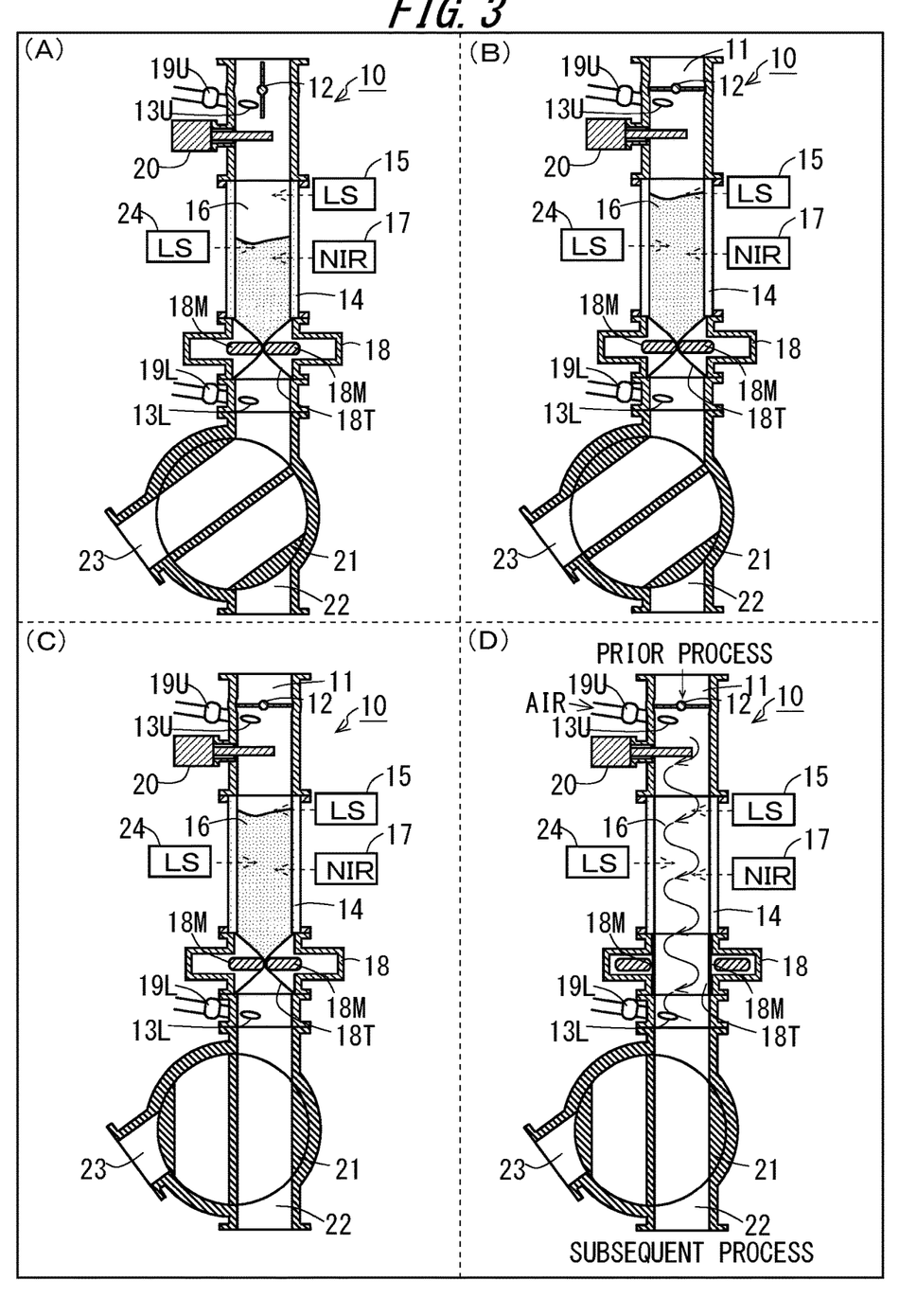
FIG. 3 is a first operation explanation diagram of the inspection and screening device.
Figure 4:
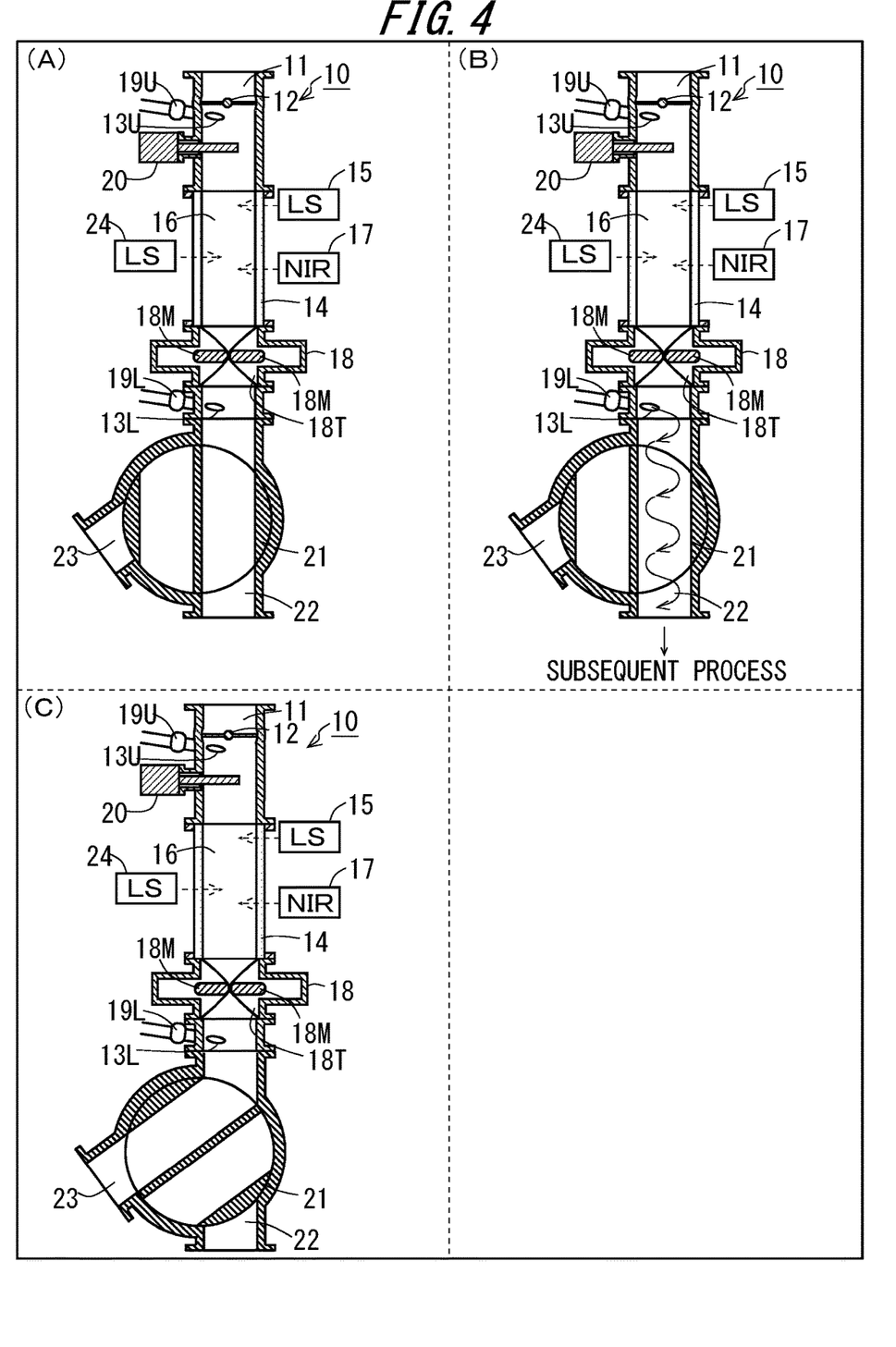
FIG. 4 is a second operation explanation diagram of the inspection and screening device.

FIG. 3 is a first operation explanation diagram of the inspection and screening device 10. Also, FIG. 4 is a second operation explanation diagram of the inspection and screening device 10. The inspection and screening device 10 is connected to the control device of the continuous production system 1. The inspection and screening device 10 performs the following operations in accordance with control signals sent from the control device of the continuous production system 1. That is to say, in the inspection and screening device 10, when raw materials are fed from the equipment connected to the upstream side of the inspection and screening device 10 in which the entrance-side gate valve 12 is in an open state and the exit-side gate valve 18 is in a closed state, the raw materials accumulate within the inspection chamber 16, as illustrated in FIG. 3(A). When the laser sensor 15 detects that the raw materials accumulated within the inspection chamber 16 have reached a predetermined height, the entrance-side gate valve 12 is closed, as illustrated in FIG. 3(B). When the entrance-side gate valve 12 is closed, inflow of new raw materials from the inlet path 11 to the inspection chamber 16 stops. The bulk density of the raw materials within the inspection chamber 16 is maintained constant while inflow of new raw materials from the inlet path 11 to the inspection chamber 16 is stopped. Accordingly, after the entrance-side gate valve 12 is closed, inspection of raw materials within the inspection chamber 16 using the spectroanalysis instrument 17 is started. If inspection using the spectroanalysis instrument 17 is performed with the entrance-side gate valve 12 in a closed state, there is no change in bulk density of the raw materials due to increase in the height of the raw materials accumulated within the inspection chamber 16, and accordingly stable inspection results can be obtained.

After inspection of the raw materials accumulated within the inspection chamber 16 is completed, switching operations of the channel switching valve 21 is performed in accordance with the inspection results. For example, in a case where the inspection results indicate that the raw materials accumulated within the inspection chamber 16 are good, the orientation of the channel switching valve 21 is switched so that the outlet channel 22, connected to the equipment to undertake the subsequently-performed processing on the raw materials accumulated within the inspection chamber 16, communicates with the inspection chamber 16, as illustrated in FIG. 3(C). Also, for example, in a case where the inspection results indicate that the raw materials accumulated within the inspection chamber 16 are defective, the orientation of the channel switching valve 21 is switched so that the outlet channel 23 for discarding the raw materials accumulated within the inspection chamber 16 communicates with the inspection chamber 16. After the switching operation of the channel switching valve 21 is complete, simultaneously with opening of the exit-side gate valve 18, or after a predetermined amount of time following the opening thereof, air blowing into the inspection chamber 16 from the opening 13U is started, and the raw materials within the inspection chamber 16 are promptly discharged from inside of the inspection chamber 16, as illustrated in FIG. 3(D).

After discharge of the raw materials is complete, the exit-side gate valve 18 is closed simultaneously with air blowing into the inspection chamber 16 from the opening 13U is stopped, as illustrated in FIG. 4(A). After the exit-side gate valve 18 is closed, whether there are any raw materials retained within the inspection chamber 16 is inspected by optical inspection using the laser sensor 24, and cleansing effects are confirmed. Also, after the exit-side gate valve 18 is closed, air blowing from the opening 13L is started as illustrated in FIG. 4(B), and the raw materials retained at the downstream side of the exit-side gate valve 18 are discharged. After a predetermined amount of time elapses from the start of air blowing from the opening 13L, air blowing from the opening 13L is stopped and the channel switching valve 21 returns to the original state, as illustrated in FIG. 4(C). The entrance-side gate valve 12 then opens again. When the entrance-side gate valve 12 opens, the raw materials that were fed from the equipment on the upstream side of the inspection and screening device 10 and that have become accumulated at the upper side of the entrance-side gate valve 12 while the entrance-side gate valve 12 was closed flow into the inspection chamber 16. Note that in a case where air blowing from the opening 13L is unnecessary due to the nature of the powder being handled or due to a reason related to the equipment structure of the inspection and screening device 10, air blowing from the opening 13L may be omitted, or the opening 13L itself may be omitted.

In the inspection and screening device 10, the above-described series of operations described by way of FIG. 3(A) through (D) and FIG. 4(A) through (C) is repeated in increments of several tens of seconds to several minutes. Accordingly, there is hardly any possibility of causing substantive trouble in continuous operations of equipment connected to the upstream side and the downstream side of the inspection and screening device 10. Inspection of the raw materials using the spectroanalysis instrument 17 is performed in a state with the entrance-side gate valve 12 closed at a predetermined height detected by the laser sensor 15, and accordingly is performed with the bulk density of the raw materials at a constant state each time. Thus, there is hardly any possibility of the measurement value of the spectroanalysis instrument 17 changing due to the bulk density of the powder. Accordingly, inspection using the inspection and screening device 10 can obtain measurement values that change depending on the bulk density of powder with good precision, in the continuous production system 1 that continuously produces tablets from powder raw materials. Also, the inspection and screening device 10 can inspect all raw materials continuously handled by the continuous production system 1 in the inspection chamber 16, and perform screening using the channel switching valve 21. Accordingly, even in a case of defects temporarily occurring in the continuous production system 1, non-defective items and defective items can be sorted in increments of the amount accumulated within the inspection chamber 16, whereby raw materials that are discarded can be maximally reduced.

An example of an overall control flow that can be realized by the continuous production system 1 in a case where the inspection and screening device 10 is disposed at sign C in FIG. 1 will be described below.

At the dryer 4 in the continuous production system 1 illustrated in FIG. 1, various types of additional raw materials are added to raw materials granulated by the granulator 3, and drying is performed. One or more heaters for performing drying by heating are provided to the dryer 4, and the amount of electricity applied to the heaters is adjusted by the control device so that the drying temperature is appropriate. The dryer 4 is also provided with a variable-speed blower, and the control device adjusts the rotational speed of the blower, so that the raw materials granulated by the granulator 3 pass through the dryer 4 at an appropriate windspeed.

Figure 5:
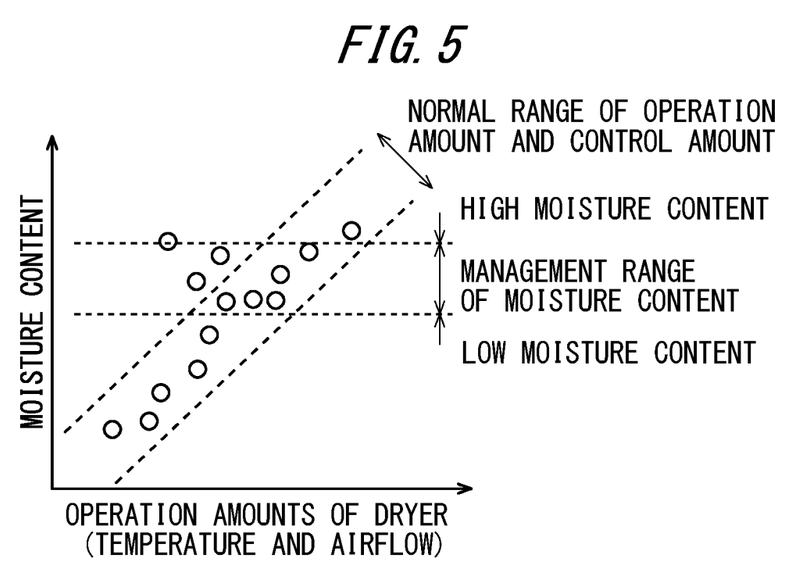
FIG. 5 is a graph illustrating an example of a correlative relation between moisture content of a raw material at an outlet of a dryer, and operation amount of the dryer.

FIG. 5 is a graph illustrating an example of a correlative relation between moisture content of raw materials at the outlet of the dryer 4 and operation amount of the dryer 4. For example, in a case where the moisture content is relatively great, the temperature of the dryer 4 needs to be set higher in accordance with the moisture content, to promote drying. Also, in a case where the moisture content is relatively small, the temperature of the dryer 4 needs to be set lower in accordance with the moisture content, to prevent excessive drying. Accordingly, feedback control is performed regarding the operation amounts of the heater and the blower at the dryer 4, in accordance with the moisture content of the raw materials exiting the dryer 4, and thus the temperature and airflow are adjusted. As long as this feedback control is appropriately performed, the moisture content of the raw materials exiting the dryer 4 will fall within a prescribed management range. Conversely, if this feedback control is not appropriately performed, the moisture content of the raw materials exiting the dryer 4 will deviate from the prescribed management range. There also are cases in which the operation amounts are deviating from a normal range due to some sort of trouble occurring in the moisture content measurement or the process, but the moisture content of the raw materials exiting the dryer 4 appear to fall within the prescribed management range. If the normal range of operation amount and control amount is determined in advance, as illustrated in FIG. 5, such moisture content measurement trouble and so forth can be detected.

Continuously measuring moisture content of powder is generally difficult in continuous production of pharmaceuticals of which raw materials are powder. However, in the inspection and screening device 10 described above, the above series of operations described by way of FIG. 3(A) through (D) and FIG. 4(A) through (C) are repeated in increments of several minutes. Accordingly, even if the inspection and screening device 10 is disposed partway along the path connecting the dryer 4 and the blender 5, there is hardly any possibility of causing substantive trouble in continuous operations of dryer 4 connected on the upstream side and the blender 5 connected on the downstream side. Inspection of the moisture content of the raw materials using the spectroanalysis instrument 17 is performed in a state in which the entrance-side gate valve 12 is closed, at a predetermined height detected by the laser sensor 15, and accordingly there is hardly any possibility of change in measurement values of moisture content occurring due to change in the bulk density of the raw materials. Accordingly, disposing the above-described inspection and screening device 10 partway along the path connecting the dryer 4 and the blender 5 in the continuous production system 1 according to the present embodiment enables feedback control of the temperature and the airflow of the dryer 4 to be performed on the basis of the moisture content of the raw materials exiting the dryer 4. Also, installing a particle size measurement device in the inspection and screening device 10 enables feedback control of the operation amount of the granulator 3 (e.g., granulation rotations, etc.) that is on the upstream side of the dryer 4, for example.

Figure 6:
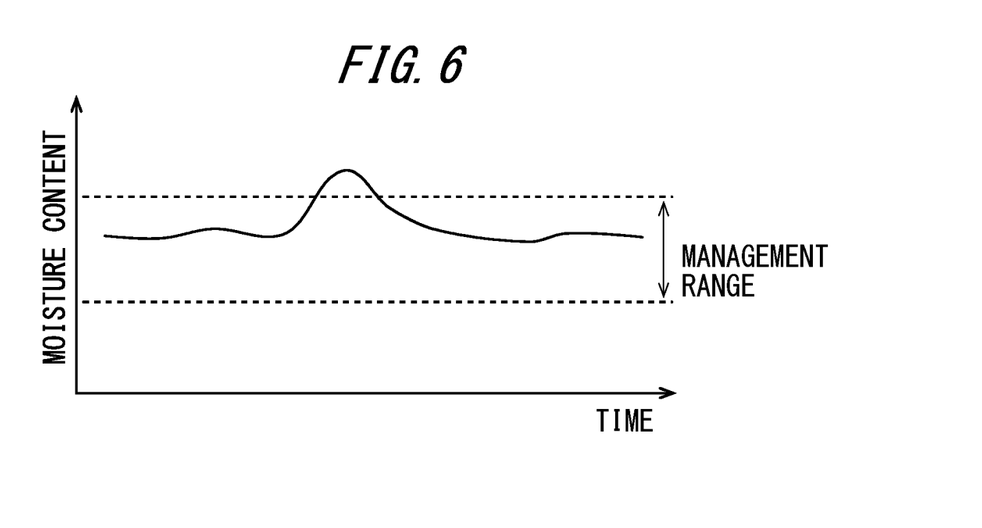
FIG. 6 is a graph illustrating an example of change in moisture content over time of a raw material that has exited the dryer.

Also, due to the channel switching valve 21 being provided to the inspection and screening device 10, disposing the above-described inspection and screening device 10 partway along the path connecting the dryer 4 and the blender 5 in the continuous production system 1 according to the present embodiment enables raw materials that are continuously processed to be discharged in accordance with inspection results. FIG. 6 is a graph illustrating an example of change in moisture content of raw materials exiting the dryer 4 over time. There is a possibility that the moisture content of the raw materials exiting the dryer 4 will temporarily deviate from the management range, as illustrated in FIG. 6, for example. In such a case, feeding the raw materials of which the moisture content deviates from the management range to the blender 5 is undesirable. However, the channel switching valve 21 is provided to the inspection and screening device 10, and accordingly, disposing the above-described inspection and screening device 10 partway along the path connecting the dryer 4 and the blender 5 enables raw materials of which the moisture content deviates from the management range in the inspection at the inspection chamber 16 to be discharged by the channel switching valve 21 to a place other than the blender 5.

Figure 7:
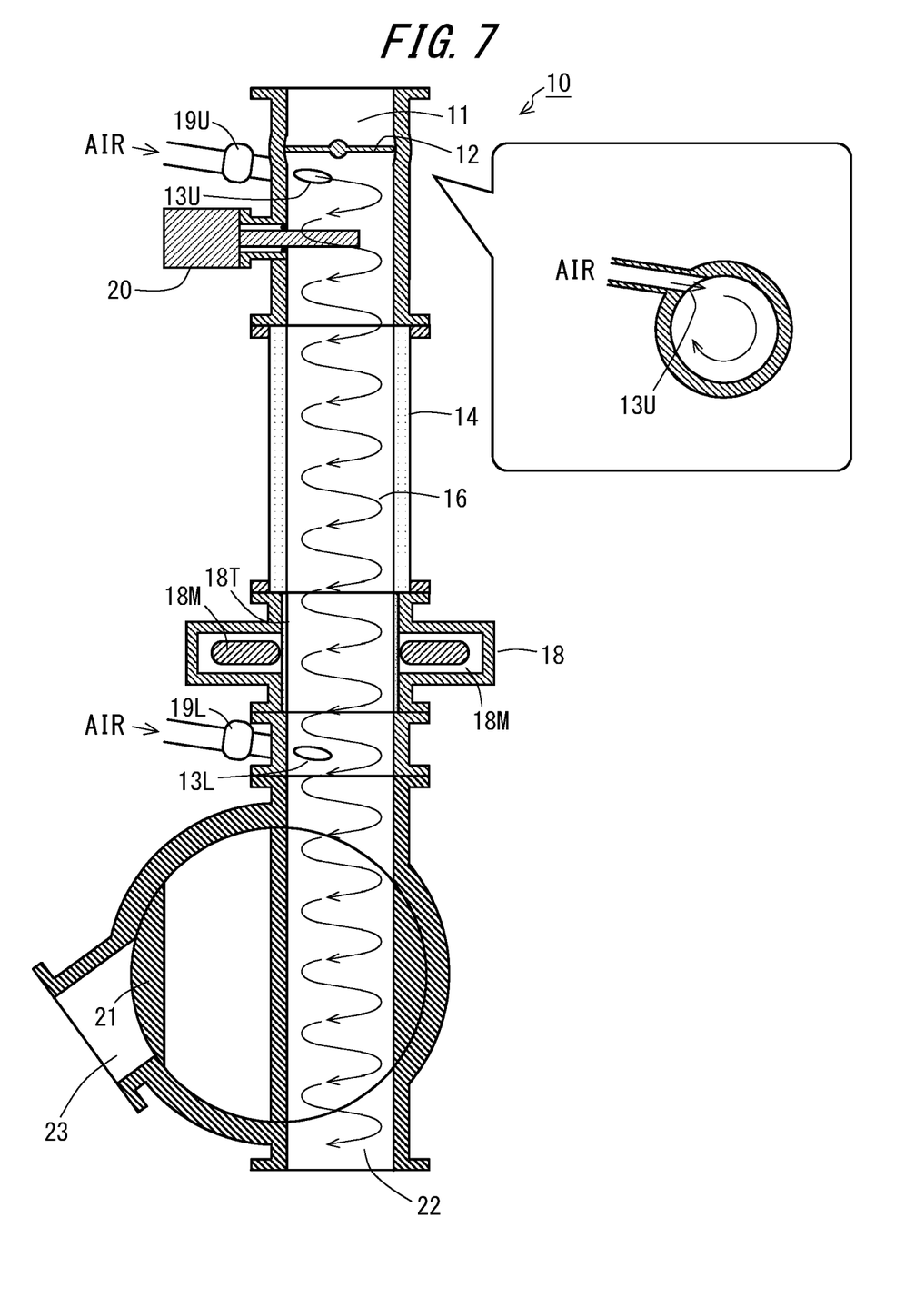
FIG. 7 is a diagram depicting an air current at the time of air blowing in the inspection and screening device.

In the inspection and screening device 10 according to the above-described embodiment, the openings 13U and 13L are formed to spray gas in a direction forming a spiral flow following the inner circumferential face of the path where the powder passes, and accordingly raw materials are not retained within the inspection chamber 16 or the like. FIG. 7 is a diagram depicting an air current at the time of air blowing in the inspection and screening device 10. The opening 13U blows gas in a direction forming a spiral flow following the inner circumferential face of the path where the powder passes directly below the entrance-side gate valve 12, and accordingly the center axis of the pipe line of high pressure air reaching the opening 13U is formed at a position close to a tangent of a circle forming the inner circumferential face of the path through which the powder passes. Thus, the air sprayed from the opening 13U becomes a spiral flow following the inner circumferential face of the path where the powder passes, which can be understood from the illustration in the balloon in FIG. 7. As a result, the inner circumferential face of the inspection chamber 16 and so forth where the powder passes is cleansed by the high-pressure air, and retained raw material powder is removed in a sure manner. Accordingly, in the inspection and screening device 10 that optically measures the quality of raw materials within the inspection chamber 16 by the spectroanalysis instrument 17 through the sight glass 14, deterioration in measurement precision of the spectroanalysis instrument 17 due to adhesion of powder to the sight glass 14 can be prevented. Note that an arrangement may be made in which confirmation of the effects of cleansing is automatically performed by optical unit through the sight glass 14, and the above series of operations described by way of FIG. 3(A) through (D) and FIG. 4(A) through (C) is performed after this confirmation.

The reasons why no powder is retained in the case of the above embodiment is as follows. That is to say, in the inspection and screening device 10 according to the above embodiment, the opening 13U is provided directly below the entrance-side gate valve 12, and accordingly around the entrance-side gate valve 12 where powder is readily retained is cleansed by high-pressure air in a sure manner. Also, in the inspection and screening device 10, air sprayed out from the opening 13U flows in a helix form, and thus air flows thoroughly throughout the path, without any low flow rate regions being formed due to stagnation of air in the path where the powder passes. Accordingly, portions at which the air for cleansing does not reach and cleansing is defective are not readily formed in the path where the powder passes. Further, in the inspection and screening device 10 according to the above embodiment, the exit-side gate valve 18 that opens and closes the path on the downstream side of the inspection chamber 16 closes off the path within the tube 18T by clamping the tube 18T, and accordingly basically does not form any structural obstructions in the powder path in the open state. Hence, around the exit-side gate valve 18 is also cleansed by air blowing by the opening 13U, performed in a state in which the exit-side gate valve 18 is open. Further, in the inspection and screening device 10 according to the above embodiment, air blowing by the opening 13L is performed after the exit-side gate valve 18 is closed, and accordingly the path between the exit-side gate valve 18 and the channel switching valve 21 is also cleansed. Thus, the continuous production system 1 according to the above embodiment can maximally suppress retention of powder in the inspection and screening device 10.

DESCRIPTION OF THE REFERENCE NUMERALS AND SYMBOLS

1 Continuous production system
2 Blender
3 Granulator
4 Dryer
5 Blender
6 Tablet press
7 Coater
10 Inspection and screening device
11 Inlet path
12 Entrance-side gate valve
13U, 13L Opening
14 Sight glass
24 Laser sensor
16 Inspection chamber
17 Spectroanalysis instrument
18 Exit-side gate valve
18T Tube
18M Opening/closing mechanism
19U, 19L Solenoid valve
20 Particle size distribution measurement device
21 Channel switching valve
22, 23 Outlet channel

The invention claimed is:

1. A continuous production system producing continuously a product from a powder of a raw material, the continuous production system comprising:
    a first processor that performs first processing on the powder of the raw material;
    a second processor that performs second processing on the powder, on which the first processor has performed the first processing;
    an inspection chamber through which powder fed from the first processor to the second processor passes; and
    a cleaner that, at a downstream side of an entrance-side gate valve that opens and closes a path connecting the first processor to the inspection chamber, sprays gas from an entrance-side opening formed on an inner face of the path in a direction forming a spiral flow following the inner face of the path,
    wherein the cleaner sprays gas from the entrance-side opening in a state in which an exit-side gate valve that opens and closes a path on an exit side of the inspection chamber is open.

2. The continuous production system according to claim 1,
    wherein the cleaner sprays gas from the entrance-side opening formed directly below the entrance-side gate valve in a direction forming a spiral flow following the inner face of the path.

3. The continuous production system according to claim 1,
    wherein the exit-side gate valve has an elastic tube that forms part of a path connecting the inspection chamber to the second processor, and a clamp that clamps the tube to close off the path within the tube, and
    wherein the cleaner sprays gas from the entrance-side opening in a state in which clamping of the tube by the clamp is released.

4. The continuous production system according to claim 1,
    wherein the cleaner further sprays gas from an exit-side opening formed directly below the exit-side gate valve in a direction forming a spiral flow following the inner face of the path.

5. The continuous production system according to claim 4,
    wherein the cleaner sprays gas from the exit-side opening in a state in which the exit-side gate valve is closed.

6. The continuous production system according to claims 3 claim 1,
    further comprising, on a further downstream side from the exit-side gate valve, a channel switch for switching a discharge path of the inspection chamber between a path connecting the inspection chamber to the second processor, and a path connecting the inspection chamber to other than the second processor.

7. A continuous production method of producing continuously a product from a powder of a raw material in a continuous production system having a first processor that performs first processing on the powder of the raw material, a second processor that performs second processing on the powder, on which the first processor has performed the first processing, and an inspection and screening device that has an inspection chamber through which powder fed from the first processor to the second processor passes,
    the method executing cleansing processing of spraying, at a downstream side of an entrance-side gate valve that opens and closes a path connecting the first processor to the inspection chamber, gas from an entrance-side opening formed on an inner face of the path in a direction forming a spiral flow following the inner face of the path,
    wherein the cleansing processing sprays gas from the entrance-side opening in a state in which an exit-side gate valve that opens and closes a path on an exit side of the inspection chamber is open.

* * * * *

UNITED STATES PATENT AND TRADEMARK OFFICE
CERTIFICATE OF CORRECTION

PATENT NO. : 11,964,446 B2
APPLICATION NO. : 17/416238
DATED : April 23, 2024
INVENTOR(S) : Akihiro Matsuki It is certified that error appears in the above-identified patent and that said Letters Patent is hereby corrected as shown below:

In the Claims

In Column 12, Claim 6, Lines 30-31, after "to" delete "claims 3".

Signed and Sealed this
Fifth Day of August, 2025

Coke Morgan Stewart
*Acting Director of the United States Patent and Trademark Office*